United States Patent
Barnea et al.

(10) Patent No.: US 11,213,784 B2
(45) Date of Patent: Jan. 4, 2022

(54) PROCESS FOR SEPARATION OF HEAVY METALS AND/OR SULFUR SPECIES FROM IONIC LIQUIDS

(71) Applicant: Clairion Ltd., Netanya (IL)

(72) Inventors: Zach Barnea, Jerusalem (IL); Eyal Barnea, Nesher (IL); Sarit Yadid, Kiryat Ata (IL)

(73) Assignee: Clairion Ltd., Netanya (IL)

( * ) Notice: Subject to any disclaimer, the term of this patent is extended or adjusted under 35 U.S.C. 154(b) by 0 days.

(21) Appl. No.: 17/047,969

(22) PCT Filed: Apr. 17, 2019

(86) PCT No.: PCT/IL2019/050443
§ 371 (c)(1),
(2) Date: Oct. 15, 2020

(87) PCT Pub. No.: WO2019/202598
PCT Pub. Date: Oct. 24, 2019

(65) Prior Publication Data
US 2021/0154618 A1  May 27, 2021

Related U.S. Application Data (60) Provisional application No. 62/659,156, filed on Apr. 18, 2018.

(51) Int. Cl.
| | |
|---|---|
| *C07D 233/58* | (2006.01) |
| *B01D 53/14* | (2006.01) |
| *B01D 53/52* | (2006.01) |
| *B01D 53/64* | (2006.01) |
| *B01D 53/78* | (2006.01) |
| *B01D 53/96* | (2006.01) |

(52) U.S. Cl.
CPC ..... *B01D 53/1425* (2013.01); *B01D 53/1468* (2013.01); *B01D 53/1493* (2013.01); *B01D 53/52* (2013.01); *B01D 53/64* (2013.01); *B01D 53/78* (2013.01); *B01D 53/96* (2013.01); *C07D 233/58* (2013.01); *B01D 2252/30* (2013.01); *B01D 2257/602* (2013.01)

(58) Field of Classification Search
CPC .......... B01D 53/14; B01D 3/34; B01D 3/343; B01D 53/02; B01D 53/1493; B01D 53/64; B01D 53/78; B01D 2251/00; B01D 2251/08; B01D 2252/30; B01D 2252/40; B01D 2252/60; B01D 2257/60; B01D 2257/602; B01D 2258/0283; C08J 11/00; C08J 11/02; B01J 8/00; B01J 10/00; B01J 19/00; B01J 2219/00; A62D 3/30; A62D 3/33; A62D 2101/43; C07D 233/58

See application file for complete search history.

(56) References Cited

U.S. PATENT DOCUMENTS

| | | |
|---|---|---|
| 4,709,118 A | 11/1987 | Yan |
| 6,350,372 B1 | 2/2002 | Degnan et al. |
| 8,501,149 B2 | 8/2013 | Felch et al. |
| 8,828,351 B2 | 9/2014 | Felch et al. |
| 9,216,393 B2 * | 12/2015 | Timken .................. B01J 31/26 |
| 9,441,172 B2 | 9/2016 | Knickerbocker et al. |
| 2008/0230445 A1 | 9/2008 | O'Brien et al. |
| 2013/0209336 A1 | 8/2013 | Harrison et al. |

FOREIGN PATENT DOCUMENTS

| | | |
|---|---|---|
| CN | 102020248 A | 4/2011 |
| CN | 106310931 A | 1/2017 |
| WO | 2009072113 A2 | 6/2009 |
| WO | 2013114350 A1 | 8/2013 |

OTHER PUBLICATIONS

Chiappe et al., "Hydrogen Sulfide and Ionic Liquids: Absorption, Separation, and Oxidation," Top Curr Chem (Z) (2017) 375:52, Apr. 26, 2017.
International Search Report for Serial No. PCT/IL2019/050443 dated Dec. 19, 2019.

* cited by examiner

*Primary Examiner* — Timothy C Vanoy
(74) *Attorney, Agent, or Firm* — McCormick, Paulding & Huber PLLC (57) ABSTRACT

Provided herein a process for purification of an ionic liquid from heavy metals, comprising combining heavy metal-containing ionic liquid and a sulfide source to form heavy metal sulfide, and separating said heavy metal sulfide from the ionic liquid.

20 Claims, 4 Drawing Sheets

PROCESS FOR SEPARATION OF HEAVY METALS AND/OR SULFUR SPECIES FROM IONIC LIQUIDS

CROSS-REFERENCE TO RELATED APPLICATIONS

This application is a National Stage application of International Patent Application No. PCT/IL2019/050443, filed on Apr. 17, 2019, which claims priority to U.S. Patent Application No. 62/659,156, filed on Apr. 18, 2018 each of which is hereby incorporated by reference in its entirety.

TECHNICAL FIELD

In one aspect the invention relates to methods for separating heavy metals and/or heavy metal residues from ionic liquids, by contacting the ionic liquids contaminated with heavy metals with a sulfide source. In a further aspect, the invention relates to methods of purifying an ionic liquid from heavy metal contaminant, particularly in regenerating spent ionic liquid used in wet scrubbers for heavy metals removal from a gas.

BACKGROUND

Heavy metals are among the most hazardous pollutants, usually associated with useful minerals and fossil fuel. Heavy metals, particularly mercury, readily vaporize upon combustion of fossil fuel and contaminate flue gases. Liquid hydrocarbons may be decontaminated prior to combustion, as disclosed e.g. in U.S. Pat. No. 4,709,118, by contacting the hydrocarbons with a specific sorbent. Additionally, liquid hydrocarbons may be decontaminated by exposing them to a large excess of sulfur compounds, and subsequently adsorbing the heavy metal sulfide on a suitable sorbent, as disclosed, e.g. in U.S. Pat. No. 6,350,372. Similarly, mercury removal from crude oil was disclosed by combining high-mercury crude and high-sulfur crude, e.g. in U.S. Pat. No. 9,441,172. Removal of heavy metals, e.g. mercury, from flue gases, by passing them through a wet scrubber comprising an oxidant, e.g. a halogen, in an ionic liquid, has been disclosed e.g. in WO patent applications WO 2009/072113 and WO 2013/114350.

The method described in WO 2009/072113 and WO 2013/114350 is based on the oxidation of the metal (e.g., $Hg^0$) by the halogen (e.g., $I_2$) and formation of the corresponding metal halide that is soluble in the ionic liquid (i.e., the scrubbing liquid). In this way the heavy metals are removed from flue gases and accumulate in the scrubbing liquid. The efficiency of the removal process drops gradually. Besides, decreasing the concentration of the oxidant as the scrubber liquid becomes more saturated with the contaminants will also decrease the efficiency of the process. Therefore, there is a need in the art to provide methods for decontamination of scrubber liquids from accumulated heavy metals, particularly of ionic liquids. There is a further need in the art to provide methods for decontamination and recovery of scrubber liquids, particularly those containing an oxidant.

SUMMARY

In one aspect of the invention there is provided a method of separating heavy metals and/or heavy metal traces from ionic liquids, by contacting the ionic liquid with a sulfide source, e.g. with hydrogen sulfide or a sulfide salt, e.g. ammonium sulfide, or sodium sulfide. The amount of sulfide required to achieve this goal may be about equimolar or in a slight excess to said heavy metals. It has been further unexpectedly found that the heavy metal sulfides, e.g. mercuric sulfide, separate out of the ionic liquid's phase; after the formation of metal sulfide, addition of water or other solvent may be required in order to remove the metal sulfide from the ionic liquid. Moreover, the separated heavy metal sulfides may be readily removed by a simple filtration without the need for special adsorbents. The heavy metal sulfides may be formed from respective heavy metal salts, e.g. from heavy metal halides.

In a further aspect there is provided a method of regenerating spent scrubbing liquid for removal of heavy metals and/or heavy metal traces from flue gases, said spent scrubbing liquid comprising an ionic liquid, a reduced oxidant species and the heavy metal, by contacting the scrubbing liquid with a sulfide source, e. g. with hydrogen sulfide or sodium/ammonium sulfide, optionally separating the resultant heavy metal sulfide, e.g. by simple filtration, regenerating said oxidant, e.g. by oxidizing the reduced form of said oxidant with a regenerating oxidizing agent, and removing water from the regenerated scrubbing liquid. It has been unexpectedly found that a reduced oxidant species, e.g. a halide ion, can be effectively oxidized into molecular halogen, and said halogen may be retained in said scrubbing liquid while water is removed, e.g. by heating and evaporation.

The invention therefore relates to a process for purification of an ionic liquid from heavy metals, comprising combining heavy metal-containing ionic liquid and a sulfide source to form heavy metal sulfide, and separating said heavy metal sulfide from the ionic liquid.

The invention also relates to a process of regeneration of spent scrubbing liquid suitable for removal of heavy metals from a gas, wherein said spent liquid comprises an ionic liquid, a heavy metal species and a reduced oxidant species, said process comprises sequentially combining said spent scrubbing liquid with a sulfide source, whereby an heavy metal sulfide is formed, and with a regenerating oxidizing agent, whereby said reduced oxidant species is regenerated into active oxidant species.

DETAILED DESCRIPTION

In one aspect of the invention there is provided a method of separating heavy metals and/or heavy metal traces from ionic liquids, by contacting the ionic liquid with a sulfide source, e.g. with hydrogen sulfide or a sulfide salt, such as ammonium sulfide or sodium sulfide.

The ionic liquid, in its most general form, is an ionic salt with a low melting point, such that it exists in the liquid state at a given temperature, preferably below 200° C. Ionic liquids possess many useful properties; in particular, these may be exceptionally good solvent for other ionic compounds, e.g. salts. Nevertheless, it has been unexpectedly found that ionic liquids that are adulterated with heavy metals and/or heavy metal salts may be effectively purified from said heavy metals by contacting them with a sulfide source, i.e. an ionic reaction with precipitation may be conducted in an ionic liquid. Moreover, precipitated heavy metal sulfide particles may be formed in an ionic liquid in an unexpectedly high particle size suitable for effective separation by a simple filtration, without the need for special adsorbents, despite the high surface-active potential of ionic liquids that may stabilize colloids and prevent aggregation. The precipitation reaction may be carried out at ambient temperature, e.g. between 15° C. and 50° C., but can also be carried out at higher temperatures.

The ionic salts (liquids) which may be purified by the process according to the invention may have a nitrogen-containing cation, e.g., quaternary ammonium cation, namely, $R^1R^2R^3R^4N^{(+)}$ wherein each of $R^1$, $R^2$, $R^3$ and $R^4$ is independently $C_1$-$C_{12}$ alkyl group (such as methyltrioctyl ammonium). Other suitable cations are positively charged nitrogen-containing rings, such as the imidazolium, pyridinium or pyrrolidinium cations, in which the nitrogen atom(s) are linked to $C_1$-$C_{12}$ alkyl groups, e.g. 1-alkyl-3-methylimidazolium (such as 1-butyl-3-methylimidazolium), 1-alkylpyridinium and N-methyl-N-alkylpyrrolidinium, wherein the alkyl group is preferably $C_2$-$C_{12}$ linear alkyl group, in particular $C_2$-$C_5$ linear alkyl group. Phosphonium cation, in which the phosphorus atom(s) are linked to $C_1$-$C_{12}$ alkyl groups, can also be considered.

Regarding the counter-anions of the ionic liquid, suitable anion is a halide, e.g. chloride, bromide and iodide. As used herein, the 1-butyl-3-methylimidazolium salts are abbreviated as [BMIM-X], wherein X indicates the counter ion, e.g., halide (especially bromide or iodide). Some of the ionic liquids are commercially available, and generally can also be synthesized by methods known in the art. For example, methyltrioctyl ammonium is commercially available in the form of its halide salts as Aliquat™ 336; the halide counter ions can be exchanged using known methods. The halide nitrogen-containing ionic liquids are generally prepared by a reaction of the nitrogen-containing moiety with a suitable alkyl halide. Synthetic methods for making halide ionic liquids are described, for example, by Lee at al. [Int. J. of Hydrogen Energy, 33, p. 6031-6036, (2008)] and Wang at al. [Acta Phys.-Chim. Sin., 21(5), p. 517-522 (2005)]. Additionally or alternatively, the ionic liquids may be prepared as set forth in WO2013/114350.

For example, the reaction of 1-methylimidazole with an alkyl halide of the formula R—X wherein R denotes an alkyl chain (preferably a linear chain) consisting of n carbon atoms (e.g., n is preferably an integer between 2 and 10) and X is chlorine, bromine or iodine, affords the corresponding 1-alkyl-3-methylimidazolium halide salt, as shown by the following reaction scheme:

$R = C_1; C_2 \ldots C_n;$
$X = Cl, Br, I$

The reactants are used in approximately equal molar amounts, or in a slight molar excess in favor of the alkyl halide. The reactants are gently refluxed at a temperature between 50 and 85° C. for about 24 to 72 hours. The formation of the ionic liquid product is accompanied by an increase at the viscosity of the reaction mixture. Upon completion of the reaction, the resultant ionic liquid is washed with a suitable solvent, e.g., diethyl ether, in order to remove residual amounts of unreacted starting materials. In this way, an ionic liquid may be obtained.

In the preferred embodiments, the ionic liquid suitable for use as described herein is hydrophilic ionic liquid. Further preferably, the hydrophilic ionic liquid is miscible with water, e.g. forms homogeneous solutions with water in all proportions, e.g. with between 1% and 80% of water.

Heavy metal contaminants that may be present in the ionic liquid prior to purification may usually be mercury, uranium, cadmium, arsenic, lead, selenium, bismuth or tin. The term "heavy metal" as used herein includes all the forms wherein said heavy metal element may be present in an oxidation state above zero, including salts, oxides, hydroxides, etc. The contamination level in the ionic liquid may be as low as several parts-per-million (ppm) or as high as 1-20% w/w, of said heavy metal or heavy metal salt. Heavy metal traces may usually be between several ppm and below 0.5% w/w.

Sulfide source suitable for the process of the present invention is usually an ionic or dissociable compound comprising or generating a sulfide anion $[S^{2-}]$. Preferably, the sulfide source is hydrogen sulfide. Other sulfide sources suitable for the processes of the invention include sulfide salts, e.g. ammonium sulfide and alkali metal sulfides. Preferably, the sulfide source is a compound that leaves no byproducts, or volatile byproducts only, such as water or ammonia, therefore some preferred sulfide sources include hydrogen sulfide and ammonium sulfide. Nevertheless, due to a large difference in the molecular weight between heavy metals and low alkali metals, e.g. sodium, even large amount of heavy metals may be removed with leaving a relatively small amount of alkali metal cations. It is assumed that these cations do not interfere with the scrubbing properties of the liquid. Therefore, some additional preferred sulfide sources include alkali metal sulfides, e.g. sodium sulfide or potassium sulfide.

Sulfide source may be provided as neat material, e.g. by adding the solid sulfide source into the contaminated ionic liquid or by purging hydrogen sulfide therethrough. Alternatively, the sulfide source may be provided as a solution in a suitable solvent miscible with the ionic liquid, e.g. the same ionic liquid, or water. The rate of addition of the sulfide source may be adjusted according to the needs of the process, e.g. the dissolution rate of the sulfide source in the ionic liquid, the heat and mass transfer efficiency, and other parameters.

Surprisingly, the amount of sulfide source required, particularly of hydrogen sulfide, may be about equimolar or in a slight molar excess to said heavy metals. Alternatively, particularly when the sulfide source is hydrogen sulfide, the amount of sulfide source may be less than equimolar, e.g. to produce a more ecology-friendly process. The amount of sulfide required may usually be no less than 70% but no more than 300% of the amount of heavy metal present in the ionic liquid. The amount of the heavy metal in the ionic liquid may be determined as known in the art prior to purification, to provide readily the required amount for the purification. Without being bound by a theory, it is believed that an ionic liquid may stabilize and activate the sulfide source, by either complex formation and/or facilitating dissociation. It is evident that little or no excess of hydrogen sulfide in the process is easier to capture and neutralize, e.g. by the means of alkali hydroxide traps or scrubbers.

Further surprisingly, it was now found that heavy metal sulfides are preferentially precipitated over heavy metal halides in an ionic liquid in presence of certain amount of water in the ionic liquid, even though the heavy metal halides are considered insoluble in water.

The heavy metal sulfides may be formed from respective heavy metal contaminants, e.g. heavy metal halides. Besides, it has been unexpectedly found that heavy metal sulfide may precipitate from the ionic liquid at a rate higher that it is re-dissolved/re-dispersed/complexated by the ionic liquid and returned into a solution. The separation of the obtained heavy metal sulfides may be readily accomplished as known in the art, e.g. by filtration through a suitable filter, e.g. vacuum filtration, gravity filtration, sedimentation by centrifugation, or separation in sedimentation tank and decantation.

In some preferred embodiments the process may be performed in an essentially water-free ionic liquid, i.e. in the presence of small amount of water or water traces. It has been found that in a presence of even minute amounts of water in the ionic liquid the separating of heavy metals is improved. Typically, the amount of water useful for improving the efficiency and the rate of the process is usually below about 15%, e.g. below about 8%, e.g. between 0.01 and 5%, or between 0.01 and 3%. Thus, in this variant of the invention heavy metal sulfide may be precipitated in, and separated from the essentially water-free ionic liquid. This variant is amenable to exploitation via a continuous process. The parameters of the process, e.g. the rate of addition of sulfide source and the time and temperature of the reaction may be adjusted such that the precipitate may be readily separated. In these embodiments, the slurry of partially decontaminated ionic liquid heavy metal sulfide may be continuously discharged to a filtration assembly, the filtrate may be analyzed for the level of decontamination and may be returned into the reaction mixture for further purification. Fresh portions of contaminated ionic liquid may be periodically or continuously added for the purification. It is believed that continuous separation of the precipitate will prevent the accumulation/re-dispersion of the heavy metal sulfide in the ionic liquid.

But sometimes the precipitate may re-disperse, e.g. after an unavoidable delay in a process. In such cases water may be added at the end of the reaction between the heavy metal and the sulfide source to form an aqueous ionic liquid mixture; water concentration may be adjusted to facilitate precipitation and/or separation of the heavy metal sulfide, and may generally reach between 25% w/w and 65% w/w of water in the ionic liquid, preferably between 35% w/w and 50% w/w. Upon completion of the precipitation of the heavy metal contaminants as sulfide salts, water may then be removed from the ionic liquid, e.g. by heating and/or evaporating at reduced pressure. The conditions for water removal may be determined based on the amount of water to be removed, the desired residual water content, and other parameters. This variant is amenable to exploitation via a batch process.

In a further aspect there is provided a method of regenerating spent scrubbing liquid for removal of heavy metals and/or heavy metal traces from flue gases, said scrubbing liquid comprising an ionic liquid, a reduced oxidant species and the heavy metal. Some ionic liquids suitable for wet scrubbers have been described in WO 2009/072113. Naturally, when a wet scrubber liquid is used up to capture heavy metals e.g. from a flue gas, its capacity to further remove heavy metals is significantly reduced with the passage of time. In some instances, the scrubbing liquid comprises an ionic liquid and an oxidant. Preferably, the oxidant is a molecular halogen, more preferably bromine or iodine. As the liquid is being used, the concentration of halogen declines, and the concentration of heavy metal halide (i.e. a salt of reduced oxidant and a heavy metal cation) increases. At some point, the spent scrubber liquid must be replaced or regenerated. It has now been surprisingly found that heavy metal cations may be separated from ionic liquid even in presence of their respective halides, by a sulfide source. Moreover, the halides can be readily oxidized into molecular halogens in the ionic liquid, and can be retained therein during evaporation of water.

The heavy metal in the scrubbing liquid is usually the heavy metal removed from flue gases, retained in the scrubbing liquid in form of an ionic compound with said reduced oxidant species. The process comprises contacting the spent scrubbing liquid with a sulfide source, e. g. with hydrogen sulfide or a sulfide salt, such as ammonium sulfide, optionally providing water to facilitate separation of heavy metal sulfide, further optionally separating the resultant heavy metal sulfide, e.g. by filtration, then regenerating said reduced oxidant, e.g. by oxidizing it with a regenerating oxidizing agent, and removing water. It has been unexpectedly found that a reduced oxidant species, e.g. a halide ion, can be effectively oxidized into molecular halogen in an ionic liquid, and said halogen may be retained in said scrubbing liquid while water is removed, e.g. by heating and evaporation. The term "spent scrubber liquid" as used herein in connection with the ionic liquid described above may usually mean that the scrubbing potential of the liquid is not complete, i.e. that the liquid has absorbed some quantity of the heavy metal and the proportional part of the oxidant species have been reduced. Spent scrubber liquid may have any residual quantity of oxidant available for further oxidation, e.g. of heavy metals. It may sometimes be desirable to decontaminate even very slightly adulterated scrubber liquid, e.g. for transportation purposes. By the way of example, some jurisdictions require that a material contain less than 260 ppm of mercury, to be considered "mercury-free" and not to impose additional restrictions on the material. Therefore, spent scrubber liquid may contain from about 1000 ppm to about 20% w/w of heavy metal prior to decontamination. Moreover, spent scrubber liquid requiring decontamination may contain a significant amount of oxidant, or even almost original amount of oxidant present, and may be useful for further scrubbing of gases of heavy metals and/or of other contaminants, e.g. gaseous sulfides, even without decontamination from heavy metals.

The separation of the heavy metal sulfides from the spent scrubbing liquid may be generally performed according to the described above for ionic liquids without the oxidizing species, e.g. halogens. For example, the preferred sulfide source is hydrogen sulfide. Heavy metal sulfide may be likewise separated by filtration, centrifugation and/or adsorption.

The oxidant species may usually be a halogen. In the scrubber liquid, the initial amount of the oxidant species may vary from about 0.1% wt to 10% wt, e.g. between 0.5 and 6% wt, or between 1.5 and 4% wt. The reduced oxidant species may usually be a halide ion. The halide ion in the ionic liquid may be oxidized with a regenerating oxidizing agent capable of oxidizing a halide into molecular halogen. In some preferred embodiments, aqueous hydrogen peroxide may be used to recover molecular halogen in the ionic liquid. Usually, the regenerating oxidizing agent has an oxidation potential higher than the reduction potential of the halide into molecular halogen. Preferably, the regenerating oxidizing agent is chosen such that it produces no byproducts, or only volatile byproducts, such as water, which can be easily removed to furnish a recovered scrubbing liquid suitable for removal of fresh portion of heavy metals from flue gases.

It may be desirable to adjust the amount of the oxidant species, e.g. halogens, in the decontaminated scrubber liquid. The adjustment may be performed by various means, e.g. by providing an oxidant species, e.g. molecular halogen, to the ionic liquid. Additionally or alternatively, reduced oxidant species may be provided to the ionic liquid prior to the oxidant recovery, e.g. providing a halide to the ionic liquid, and then providing a regenerating oxidizing agent.

The recovery may optionally be performed at a temperature of between 20° C. and 85° C., e.g. between 20° C. and 30° C., such as room temperature. Water may then be evaporated, e.g. at elevated temperature, without loss of regenerated halogen. The evaporation temperature may vary broadly, optionally under reduced pressure, e.g. between 50 and 98° C., for example between 75 and 98° C. under atmospheric pressure, or between 65 and 75° C. under reduced pressure.

Figure 1:
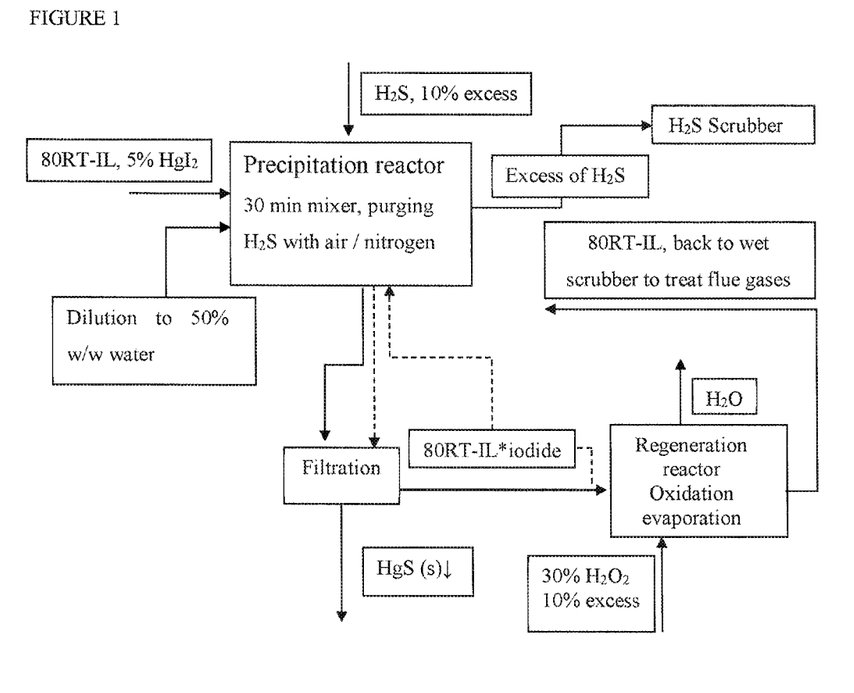
FIG. 1 shows an exemplary flow chart of a process according to an embodiment of the invention.

A schematic flow chart of the process of regeneration of an adulterated scrubber liquid according to one embodiment of the invention is demonstrated in FIG. 1. The process may be carried out in a batch mode or in continuous mode, indicated by solid arrows or dashed arrows, respectively.

Starting with a batch variant, there is provided spent scrubber liquid containing, by the way of example, an ionic liquid with 5% wt of mercuric iodide, denoted as "80RT-IL, 5% $HgI_2$". The spent scrubber liquid is fed into a precipitation reactor, denoted "Precipitation reactor", and hydrogen sulfide is fed to the reactor either in gaseous form or dissolved in a carrier (denoted "$H_2S$, 10% excess"). The reaction mixture is then mixed, e.g. for 30 minutes (denoted "30 min mixer"). During this time interval mercuric sulfide is allowed to form and optionally to re-disperse. Thereafter, water is added to the reaction mixture in the precipitation reactor, e.g. to final concentration of 50% wt, to effect precipitation of mercuric sulfide from aqueous ionic liquid mixture (denoted "Dilution to 50% w/w water"). Mercuric sulfide (denoted "HgS (s)↓") is then separated (denoted "Filtration") from the reaction mixture, and the filtrate is directed for regeneration.

In a continuous filtration process, as denoted by dashed lines, a portion of the reaction mixture with partially precipitated mercuric sulfide in the precipitation reactor is continuously discharged from the precipitation reactor, and the mercuric sulfide (denoted "HgS (s)↓") is then continuously separated (denoted "Filtration") from the reaction mixture. The filtrate (denoted "80RT-IL*iodide") may then be recycled into the precipitation reactor for further decontamination, or, based on target heavy metal separation efficiency, directed to regeneration.

Regarding the regeneration step, if the decontaminated spent scrubber liquid (denoted "80RT-IL*iodide") contains target levels of mercury or below, it is transferred into a regeneration reactor (denoted "Regeneration reactor"), wherein an oxidizing agent is provided, e.g. hydrogen peroxide (denoted "30% $H_2O_2$" and "10% excess"). The regeneration of the spent liquid then occurs (denoted "Oxidation"), and the excess of water is removed (denoted "$H_2O$" and "evaporation"). The regenerated scrubber liquid may then be returned to the wet scrubber process to treat flue gases (denoted "80RT-IL, back to wet scrubber to treat flue gases").

The excess of hydrogen sulfide is removed by purging air or nitrogen through the reaction mixture in the precipitation reactor (denoted by "purging $H_2S$ with air/nitrogen" in the "Precipitation reactor" box). The removed excess of hydrogen sulfide (denoted "Excess of $H_2S$") is trapped in a scrubber to prevent the release into the environment (denoted "$H_2S$ scrubber").

In an additional aspect provided herein a method for removing sulfides from a gaseous stream, by absorbing and/or dissolving a sulfide in a hydrophilic ionic liquid, e.g. in presence of an oxidant. Upon addition of water, the oxidation of sulfide takes place and separable reaction products may be obtained (e.g. elemental sulfur). The process enables the decontamination of a gaseous stream from sulfides, e.g. hydrogen sulfide, i.e. by passing the stream through a wet scrubbing liquid, comprising an ionic liquid and an oxidant, preferably an essentially water-free water-miscible ionic liquid, and adding water to the ionic liquid. As long as the addition of water is performed in presence of an oxidant, the sulfides are converted into elemental sulfur and/or sulfates. Preferably, the oxidant is a halogen, e.g. chlorine, bromine or iodine. Advantageously, the process may be performed as atmospheric pressure.

Gaseous sulfides, e.g. hydrogen sulfide, can only be absorbed in the ionic liquid containing little or no water, e.g. no more than 15% wt (it is known that the interaction of ionic liquid with $H_2S$ is stronger than with water, as mentioned inter alia, in a recent review article describing the use of ionic liquids in scrubbing gaseous sulfides, by Chiappe and Pomelli, in Top Curr Chem (Z) (2017) 375:52, doi 10.1007/s41061-017-0140-9O). Moreover, as demonstrated in the examples below, halogens cannot oxidize sulfides with any appreciable efficiency in the ionic liquids containing no or only small amounts of water, e.g. up to 15% wt, but with enhanced aqueous environment sulfides are effectively oxidized into elemental sulfur and/or sulfates, in the ionic liquids. Processes for scrubbing hydrogen sulfide gas in an aqueous iodine solution at high pressure and high temperature were disclosed, e.g. in U.S. Pat. Nos. 8,501,149, and 8,828,351. Processes for scavenging mercaptans in liquid phase with transition-metal oxidants in aqueous solutions of quaternary ammonium compounds are disclosed, e.g. in US patent application 20080230445. Similarly, processes for desulfurization of gases were disclosed in Chinese patent CN102020248, utilizing hydrophobic ionic liquid and iron; and in Chinese patent CN106310931 (desulfurization and deamination).

An operation of a wet scrubber comprising an oxidant, e.g. a halogen, in an ionic liquid, is described in detail in WO patent applications WO 2009/072113 and WO 2013/114350. Such wet scrubbers are also useful for conducting the processes of the present invention, namely decontamination of gaseous streams, at temperatures from ambience temperature to about 150° C. In contrast to water-based scrubbing liquids, the processes of the present invention allow operating scrubbers at higher temperatures, since the ionic liquids used for the processes possess negligible vapor pressure and high thermal stability.

Water may be added to the ionic liquid, to effect the oxidation of captured sulfides in the ionic liquid by the oxidant. The concentration of water may vary, e.g. between 15 and 60 weight percent. The solid elemental sulfur formed in the process may be separated from the ionic liquid by filtration or centrifugation, as described herein, and the excess of water may be evaporated, e.g. at elevated temperature and/or reduced pressure.

Preferably, the oxidant is present in the ionic liquid during the capture of the sulfide from the gaseous stream. The oxidant species may usually be a halogen. In the ionic liquid used for capture of sulfide, the initial amount of the oxidant species may vary from about 0.1% wt to 10% wt, e.g. between 0.5 and 6% wt, or between 1.5 and 4% wt. Generally, the oxidant may be added into the ionic liquid at any stage prior to adding of water, e.g. before the oxidation may occur. Alternatively, the oxidant may be added as an aqueous solution, concomitantly with the addition of water, e.g. as a polyhalide compound, such as triiodide ($I_3^{(-)}$) compound or tribromide ($Br_3^{(-)}$) compound, to the ionic liquid containing absorbed/dissolved sulfide.

Figure 2:
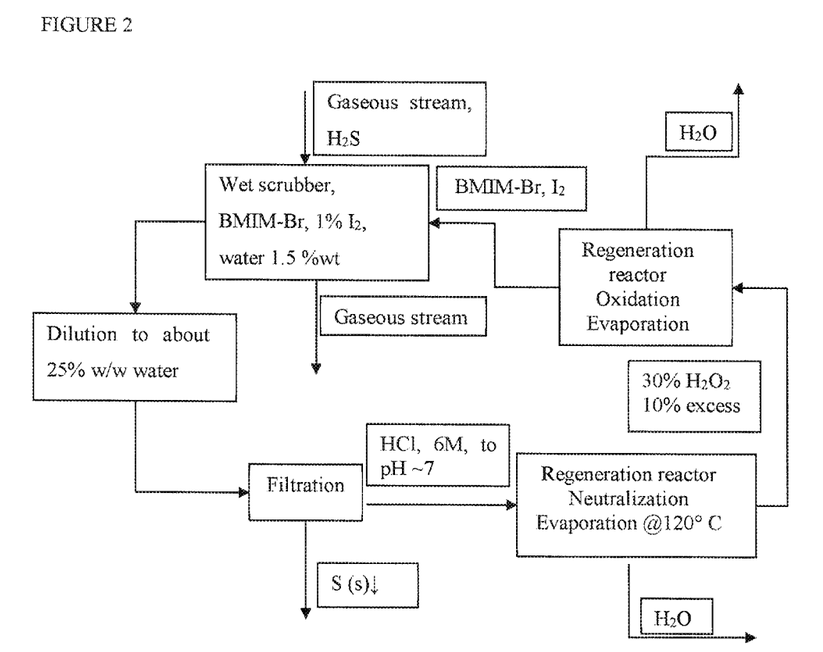
FIG. 2 shows a further exemplary flow chart of a process according to an embodiment of the invention.

A schematic flow chart of the process of scrubbing of a gaseous stream from hydrogen sulfide and regeneration of a spent scrubber liquid according to one embodiment of the invention is demonstrated in FIG. 2.

A wet scrubber, denoted as "Wet scrubber, BMIM-Br, 1% $I_2$, water 1.5% wt", is being fed with a gaseous stream containing hydrogen sulfide, denoted as "Gaseous stream, $H_2S$", and a decontaminated stream leaves the scrubber, denoted as "Gaseous stream". At least a portion of the scrubbing liquid may be removed from the scrubber, either continuously or discretely, and diluted with water, to exemplary concentration of about 25% wt of water in the ionic liquid, denoted as "Dilution to about 25% w/w water". The oxidation of the absorbed hydrogen sulfide then occurs, and elemental sulfur solid is formed. The liquid is then being fed into a filtration facility (denoted "Filtration"), to separate the solid sulfur from the ionic liquid (denoted "$S_{(S)}\downarrow$"). The liquid is then transferred into a regeneration reactor, denoted "Regeneration reactor, Neutralization, Evaporation @120° C.", and a step of neutralization is performed (denoted "HCl, 6M, to pH ~7"), followed by evaporation of water (denoted "$H_2O$"). The dried neutralized scrubbing liquid is then regenerated (denoted "Regeneration reactor, Oxidation, Evaporation"), by the addition of hydrogen peroxide (denoted "30% $H_2O_2$, 10% excess"), and the ionic liquid is being dried to acceptable levels of residual water (denoted "$H_2O$"), before being returned into the process (denoted "BMIM-Br, $I_2$").

Briefly, in the cases when a certain amount of oxidant remains in the scrubber liquid contaminated with heavy metals, the excess of a sulfide from the process of decontamination of the ionic liquid from the heavy metals, may be likewise removed by direct transfer of the liquid to the precipitation reactor, e.g. adding water.

Additionally, the invention offers an elegant way to combine the removal of the heavy metals and sulfides concomitantly from a contaminated gaseous stream, in a single process based on two discrete steps, exploiting the dependence of sulfides absorption and oxidation on the presence of water in the ionic liquid, as described in greater detail below. Therefore, according to a further aspect of the invention provided herein a process for capturing sulfides and heavy metals from a gaseous stream, comprising the steps of:

passing the gaseous stream through a scrubbing liquid comprising water-free, water-miscible ionic liquid and an oxidant reducible to halide, e.g. a halogen, and introducing water, either in the presence of indigenously formed heavy metal halide or of an added heavy metal halide.

Upon introduction of water, heavy metal sulfides may be more easily separated, and excess sulfides may be converted into elemental sulfur and/or sulfates. Absorbed sulfide from the gaseous stream may thereby be acting as a decontamination aid for the spent scrubber liquids contaminated with heavy metals, and the captured heavy metals, e.g. in a halide form, may thereby aid in capturing sulfide from the gaseous stream.

Advantageously, the process may be carried out at atmospheric (ambient) pressure.

Without being bound by a theory, it is believed that when a heavy metal is passed through the scrubbing liquid, the oxidant reducible to a halide oxidizes the heavy metal to corresponding heavy metal halide. This indigenously formed heavy metal halide (i.e. heavy metal salt formed in the process of decontamination of the gas from heavy metals) may then react with a sulfide absorbed in the essentially water-free water-miscible ionic liquid, to form corresponding heavy metal sulfide. When the molar amount of heavy metal is significantly higher than the molar amount of sulfide, the amount of indigenously formed heavy metal halide may be sufficient to trap the sulfide in the gaseous stream. In these cases, prior to adding water, an additional amount of sulfide may be added, to effect the conversion of heavy metal halides to sulfides. Therefore the process may further comprise determining if a molar ratio between said heavy metal halide and sulfide is higher than 1, determining the amount of sulfide required to bring the ratio to below 1, and adding the determined amount of sulfide into said mixture, prior to adding of water. This way the heavy metal will be removed from the scrubbing liquid and no excess of heavy metal halide will be formed. When the molar amount of heavy metal is significantly lower than that of sulfide, heavy metal halide may be added externally to the scrubbing liquid to assist in more effective capturing of sulfide. The heavy metal halide may be obtained, e.g. from other heavy-metal treatment processes.

It is also assumed that the kinetics of formation of heavy metal sulfide is significantly more rapid than the oxidation of sulfide by the oxidant, particularly when little or no free water is present. The heavy metal is being thus captured by the oxidant, and the sulfide is being captured by the heavy metal, whereas the excess of captured sulfide is readily converted to elemental sulfur upon addition of water, which simultaneously induces the precipitation of heavy metal sulfide. Variation of the water content of the system from essentially water-free ionic liquid to aqueous ionic liquid enables sulfide absorption in the water free system, and subsequently upon adding water for the purpose of precipitation of heavy metal sulfides, also the oxidation of free sulfide. The advantages of the process include that it may eliminate the need of an additional sulfide scrubber at some applications.

The oxidant is preferably is chosen such that it is reducible into a halide, e.g. that at least one of its reduced species is a halide. The oxidant may thus be a halogen, preferably iodine or bromine, but chlorine may also be suitable.

In the aspects where sulfide is to be removed from the ionic liquid, the decontamination process may comprise, in presence of an oxidant or oxidant residues, steps of adding water, preferably to final concentration of water between about 10% wt and 60% wt, e.g. between 15 and 60% wt, as described above, and filtration off of the elemental sulfur and/or heavy metals' sulfides. The ionic/scrubbing liquid may be regenerated, e.g. by a process comprising steps of combining the decontaminated scrubbing liquid with a regenerating oxidizing agent, e.g. ozone or a peroxide, and optionally with an acid, e.g. to bring the pH values to below 7, and evaporating the water, e.g. to the concentration of below about 5%.

The ionic liquid and the heavy metal salts that may be used in the process are essentially the same as described above. Halogen may be bromine or iodine. As demonstrated in the Examples below, these are suitable halogens for the present purpose, as, quite unexpectedly, even bromine does not evaporate during the scrubbing process and passing of a gas through the liquid at ambient pressure. The capturing of sulfide gases and/or heavy metals may be therefore advantageously carried out as described above without significant adaptations.

For the purification of the scrubbing liquid after capturing sulfides and/or heavy metals, water may be added. The remaining oxidant of the scrubbing liquid may then oxidize the sulfides into elemental sulfur and/or sulfates. Elemental sulfur and/or heavy metal sulfides may then be advantageously removed, e.g. by filtration, or centrifugation and decantation. The amount of water to effect the oxidation of sulfides may be above about 10%, and may also be above 15% wt, or above 30% wt, but should generally be between 15% wt and 60% wt. The higher the water concentration, it is believed that the separation, e.g. by filtration/centrifugation, would be more readily performed. Other separation methods may also be suitable.

The oxidant may be readily regenerated from the halide form, e.g. by adding a regenerating oxidizing agent, as described generally above when the oxidant is a halogen. The regenerating oxidizing agent suitable for the present processes may be ozone or hydrogen peroxide. Usually, the regenerating oxidizing agent has an oxidation potential higher than the reduction potential of the halide into molecular halogen. Additionally, the amount of the oxidant in the liquid may be adjusted, as described generally above.

Sometimes it may be necessary to adjust the pH, e.g. to add an acid. Generally, the desired pH is dependent on the regenerating oxidant species and on the specific pH requirements. For example, when the regenerating oxidant is iodine (and hydrogen peroxide is added in order to oxidize iodide to iodine), the pH should be adjusted to between 1 and 7, preferably to between 3 and 7, or to between 4 and 6.

Finally, water may be removed by evaporation, e.g. at elevated temperatures, to a final concentration of below about 7% wt, e.g. below 4% wt, below 2.5% wt, or below 1.5% wt, e.g. to about 1.1-1.5% wt of water; the temperature may vary as described above, to obtain the regenerated ionic liquid.

Hence, the invention enables the recycling of a spent scrubbing liquid that was treated as described above by the additional following steps: reducing the pH of the ionic liquid to below 7, oxidizing the halide into elemental halogen with the aid of a regenerating oxidizing agent, and removing water from the ionic liquid.

EXAMPLES

Materials

The ionic liquid 1-butyl-3-methylimidazolium bromide, 99.8% purity, was purchased from Chemada, Israel. Mercuric iodide, 98% purity, was purchased from Sigma Aldrich. $H_2S$ 99% purity, was purchased from Gas Technology. Ammonium sulfide, 95% purity, was purchased from Sigma Aldrich. Hydrogen peroxide, 30%, was purchased from BioLab, Israel, Sodium sulfide 35% $Na_2S$ was purchased from Merck, Bromine 99.9% was purchased from Sigma Aldrich, Sodium hydroxide and hydrochloric acid 37% was purchased from BioLab Israel.

Example 1—Separation of Mercury from Ionic Liquid with Hydrogen Sulfide

To demonstrate the recycling efficiency of an ionic liquid that can be used in wet scrubber applications for mercury removal from flue gases, contaminated ionic liquid was prepared. The liquid was 1-butyl-3-methylimidazolium bromide (BMIM-Br) with water, adulterated with mercuric iodide ($HgI_2$), as follows.

BMIM-Br, 296 grams, was placed into a 500-mL round-bottom three-necked flask, followed by 10.5 grams of water. The liquid was mixed till dissolution using mechanical overhead mixer with Teflon® blade. Towards the end of dissolution the apparent viscosity of the solution was increased. Thereafter, mercuric iodide, 46.2 grams, was added and mixed until dissolution, resulting in decrease of the viscosity back to normal.

The experimental system was built as follows: hydrogen sulfide gas cylinder was connected via a rotameter to the three-necked flask, equipped with an immersion thermometer and a reflux condenser. The outlet of the reflux condenser was connected to a series of three traps to avoid emission of hydrogen sulfide into the atmosphere.

Hydrogen sulfide was supplied continuously. The following observations were made. After 6 minutes a black precipitate was formed. After 11 minutes the reaction mixture turned into a black slurry and the apparent viscosity increased. After 21 minutes black color disappeared, and a clear colloid was obtained with light brown color, which at 28 minutes was observed as orange and did not change until the end of the reaction.

At the end of the reaction the mixture was heated on water bath to 40° C., and dry nitrogen was further purged through the mixture for 40 minutes to expel the excess of hydrogen sulfide.

A portion of 145.3 grams of the mixture was diluted with 132.6 grams of water to furnish the final concentration of about 50% of water in the solvent and stirred on a shaker for few minutes. The color of the mixture changed rapidly to black, and the mixture was left without stirring overnight to effect precipitation. Separation was observed.

An aliquot of 14.2 grams of the supernatant was filtered with a syringe 0.22 μm, and was analyzed for mercury and sulfur content. The content found was 0.0589% for mercury whereof only 190 ppm were attributed to mercuric iodide, and 63.6 ppm for sulfur.

The remainder of the liquid, 263.7 grams, was filtered off with a vacuum filtration on 20 m paper filters, to obtain 232.8 grams of filtrate. The cake was washed with 100 grams of water and 50 grams of isopropanol, and then dried at 70° C. for 48 hours. The final weight of the cake was 17.1 grams. The elemental composition of the cake was 7.38% S, 54% Hg, and the rest the adsorbed liquid.

Iodide was recovered into molecular iodine by adding to 82 grams of the filtrate about 1.5 grams of 50% w/v solution of hydrogen peroxide. The color changed immediately to dark brown. Water was evaporated at 70° C. for at rotary evaporator, to yield BMIM-Br iodine solution, which can be used for removing of mercury from flue gases.

Figure 3:
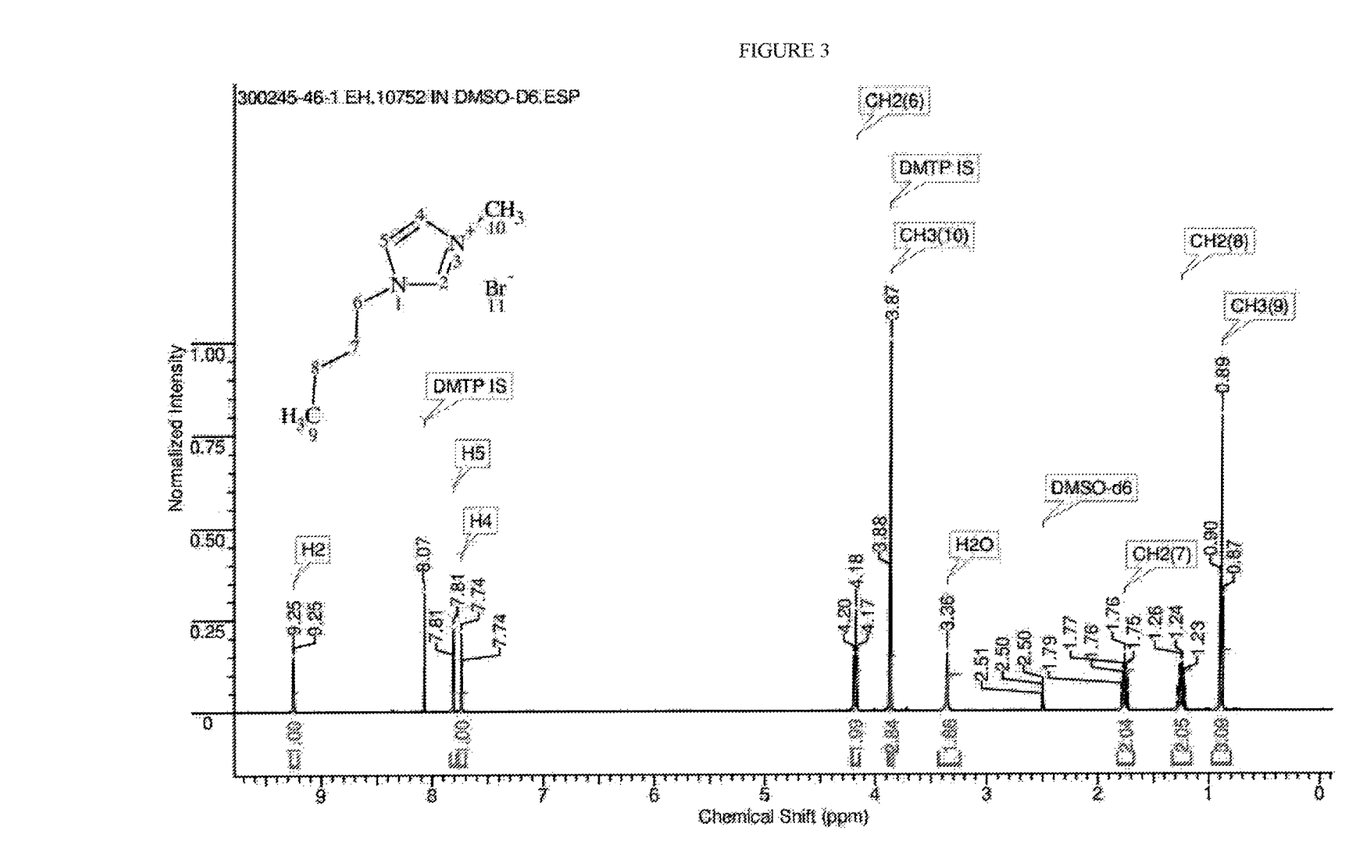
FIG. 3 shows an NMR spectrum of an ionic liquid suitable for use as a heavy metal scrubber liquid.
Figure 4:
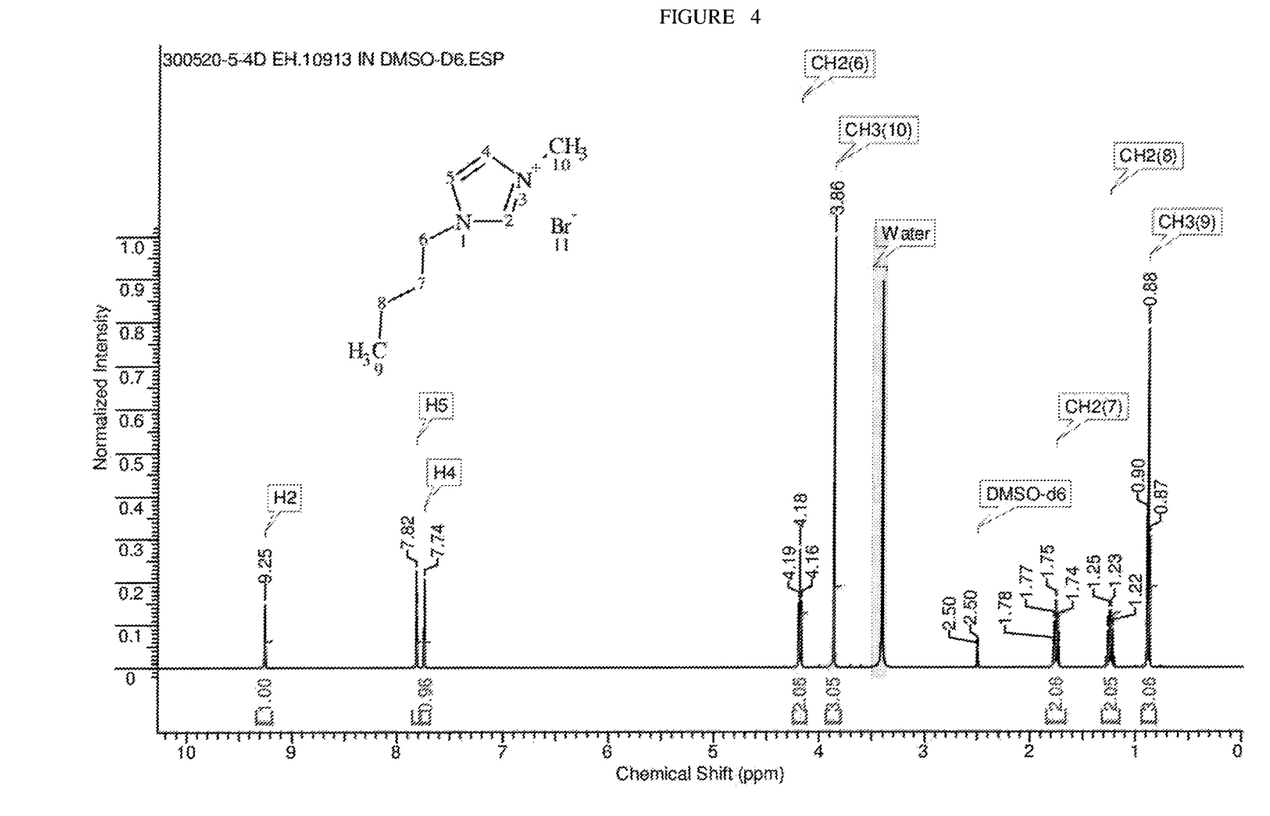
FIG. 4 shows an NMR spectrum of the regenerated ionic liquid, which is the ionic liquid which spectrum is shown in the FIG. 3, after purposeful adulteration and regeneration.

The chemical composition of the scrubber liquid before use and after regeneration was followed by the $^1$H-NMR spectra of the liquid, as demonstrated in the FIGS. 3 and 4, before use and after regeneration, respectively. Briefly, about 60 mg of accurately weighed sample was dissolved in 950 microliters of deuterated dimethyl sulfoxide. Additionally, about 2.5 mg of dimethyl terephthalate (Sigma, cat #86440) were added in 50 microliters of solution (about 50.137 mg/mL) to the sample, for quantitative determination of water. Identical spectra were obtained, signifying that the regeneration did not alter the chemical composition of the scrubber liquid. The spectra contained a triplet at 0.89 ppm, a sextet at 1.24 ppm, a quintet at 1.76 ppm, a broad singlet at 3.36 ppm (water), a singlet at 3.87 ppm, a triplet at 4.18 ppm, a triplet at 7.74 ppm, and a singlet at 9.25 ppm.

Example 2—Separation of Mercury from Ionic Liquid with Sodium Sulfide

Ionic liquid, contaminated with mercury, can also be decontaminated without using hydrogen sulfide.

The ionic liquid was 1-butyl-3-methylimidazolium bromide (BMIM-Br), adulterated with mercuric iodide ($HgI_2$). The amount of about 0.364 gr of mercuric iodide was dissolved in 15.05 gr of the ionic liquid at room temperature.

An amount of 0.215 gr of sodium sulfide hexahydrate (35% $Na_2S$) was added to the ionic liquid, followed by 30 mL of water. A dark red precipitate was formed, which turned black in several minutes. The precipitate was separated by gravitational filtration on a filter paper.

Iodide was recovered into molecular iodine by adding about 0.4 g of 35% w/v solution of hydrogen peroxide and 5.8 ml 1 N HCl, and water was evaporated at 70° C. at rotary evaporator.

Example 3—Separation of Mercury from Ionic Liquid with Ammonium Sulfide

The ionic liquid was 1-butyl-3-methylimidazolium bromide (BMIM-Br), adulterated with mercuric iodide ($HgI_2$). The amount of about 100 mg of mercuric iodide was dissolved in 2 mL of the ionic liquid at room temperature.

Ammonium sulfide solution was prepared at concentration of 20% w/v in water. About 1 g of the solution was transferred into the ionic liquid. A dark red precipitate was formed, which turned black in several minutes. The precipitate was separated by gravitational filtration on a filter paper.

Iodide was partially recovered into molecular iodine by adding about 0.4 g of 10% w/v solution of hydrogen peroxide, and water was evaporated at 70° C. at rotary evaporator.

Example 4—Separation of Sulfur from Ionic Liquid after Iodine Oxidation of Sodium Sulfide The ionic liquid containing iodine was 1-butyl-3-methylimidazolium bromide (BMIM-Br), comprising about 3.6% wt iodine ($I_2$). The amount of about 0.161 gr of iodine was dissolved in 4.3 gr of the ionic liquid at room temperature.

An amount of 0.141 gr of sodium sulfide were added into the ionic liquid solution. Thereafter, a 1 mL of water was added into the IL. A yellow precipitate was formed. Additional 3.3 mL of water were added to the mixture and the precipitate was separated by gravitational filtration on a filter paper. The solid was filtered and weighed: 0.06 gr of wet elemental sulfur was found.

Iodine was recovered by adding about 0.1 g of 35% w/v solution of hydrogen peroxide, and water was evaporated at 90° C.

The soluble sulfur ions' (sulfite/sulfate) concentrations within the ionic liquid were tested. The concentration was analyzed by oxidation of all sulfur into sulfate by addition of hydrogen peroxide and sulfate was analyzing with PF-12 photometer (manufactured by Macherey Nagel, sulfate visocolor test kit). The results indicate about 99% of the $S^{-2}$ removal from the IL.

Example 5—Absorption of Hydrogen Sulfide by Ionic Liquid with Bromine Oxidation (BMIM-Br $Br_2$-1%)

Experimental setup contained an air supply, connected to hydrogen sulfide generator (sulfide—hydrochloric acid setup), followed by 2 scrubbers, the first one experimental and the second contained access of alkali hydroxide to capture hydrogen sulfide that might escape the first scrubber. Briefly, Scrubber 1 contained ionic liquid 1-butyl-3-methylimidazolium bromide (BMIM-Br) comprising bromine ($Br_2$). The amount of about 0.906 gr of bromine was dissolved in 89.7 gr of the ionic liquid at room temperature than about 2.92 gr of water was added into the mixture. Scrubber 2 contained sulfide scrubbing liquid to capture $H_2S$ that was not absorbed within the IL scrubber. The liquid contained 26.4 gr of NaOH solution (1 N) in 68 gr of water.

$H_2S$ generator: 1.46 g of ammonium sulfide solution (44% $(NH_4)_2S$) were mixed with 19.5 mL of water and added into three-necked flask. One inlet was equipped with a pressure equalizing cylindrical funnel filled with a solution of 10.78 gr of 1 N HCl and 23 gr of water. The second inlet was connected to the air cylinder (in order to wash $H_2S$ out from the flask), equipped with a rotameter. The air cylinder was 30-L of 99.99% dry Air, manufactured by Oxygen and Argon Works Ltd. The third outlet was connected to the scrubber 1.

Test procedure: The air flow was set of 0.06 LPM and kept constant during the test. The HCl was added dropwise into the ammonium sulfide solution at a continuous rate during 1.5 hr, to furnish a calculated $H_2S$ concentration in gas of about 26,000 ppm. The gas that was thus generated by the reaction of ammonium sulfide and hydrochloric acid was passed from the $H_2S$ generator into scrubber 1 (IL), and then into the scrubber 2 in order to collect $H_2S$ residues.

At the end of the test, 86 mL of water were added into scrubber 1 (into IL). White/gray solid was formed, that was filtered off by vacuum filtration, yielding about 0.06 gr of sulfur powder. Thereafter, the filtrate ionic liquid from scrubber 1 was transferred into 250 mL beaker and heated to 95° C., in order to evaporate the water that was added.

Bromide was recycled into molecular bromine by oxidation with ozone. The oxidation was performed using ozone that was passed through the solution. The ozone was generated by AC-500 Ozone Generator, manufactured by Ozone Solutions, using dry air flow over the generator at 50 mL per minute for 45 min (about 0.15 gr O3). Bromine reactivation was followed by UV-Vis spectrophotometer, during the oxidation.

The sulfate contents within the ionic liquid (scrubber 1) and within scrubber 2 were analyzed by PF-12 photometer Macherey Nagel $SO_4$ testing kit (visocolor sulfate test kit). About 0.07 gr of S-equivalent was found within the liquid. Scrubber 2 liquid was likewise analyzed for sulfate content. An amount of 4 gr of hydrogen peroxide solution (30% w/w) and 6 gr of hydrochloric acid solution (4 M) were added in order to oxidize sulfur moieties into sulfate. The results are summarized as elementary sulfur equivalent weight in the Table 1 below.

TABLE 1

| S filtrate as an elementary S gr | S as a sulfate in the IL gr | S as a sulfate in scrubber 2 gr | % S absorbed in IL % |
|---|---|---|---|
| 0.06 | 0.07 | 0.068 | 66 |

It can be seen from this and the preceding example 4 that halogen can be recycled back to be available for reaction and further absorption of $H_2S$ or mercury. Overall, the substance that was consumed in the process was hydrogen peroxide in the case of iodine (Example 4), and ozone in the case of bromine (Example 5).

Example 6—Absorption of Hydrogen Sulfide by Ionic Liquid with Iodine Oxidation (BMIM-Br $I_2$-5%) with Varying Amount of Water The general setup and the experimental procedure are as described for the Example 5 above. Generally, scrubber 1 contained ionic liquid 1-butyl-3-methylimidazolium bromide (BMIM-Br) and iodine ($I_2$). The amount of 1.25 gr of iodine was dissolved in 24.5 gr of the ionic liquid at room temperature. When no additional water was introduced (example 6a), the content of water was about 1.2% wt. When 2.1 g of water were additionally introduced (example 6b), the final content of water was about 7.6% wt.

Scrubber 2 contained: 6A: a mixture of 7.28 gr of NaOH (1 N) solution in 144 gr of water; 6B: a mixture of 8.6 gr of NaOH (1 N) solution in 136 gr of water.

$H_2S$ generator contained 0.47 g of ammonium sulfide solution (44% wt $(NH_4)_2S$) with 15.7 ml water. Acid solution was made up with 6.7 gr of 1 N HCl and 34.6 water.

Air flow was set to 0.040 LPM (Example 6A), or 0.070 LPM (Example 6B), and kept constant during the test. The HCl was added dropwise into the ammonium sulfide solution at a continuous rate during 3 hr, to furnish a calculated $H_2S$ concentration in gas of about 11,000 ppm (Example 6A), or for 2 hr and 23,000 ppm (Example 6B).

At the end of the test, 7.2 mL of water was added into scrubber 1, to final water concentration of about 23.8% w/w (Example 6A), or 7.0 mL of water to 24.0% wt (Example 6B). Yellow solid was formed and filtered by vacuum filtration (Examples 6A and 6B).

The sulfate content was analyzed as in the Example 5, the results are shown as elementary sulfur equivalent weight in the Table 2 below.

From the result one can see that increasing water percentage within the IL decreases $H_2S$ absorption efficiency.

TABLE 2

| Example | S filtrate as an elementary S gr | S as a sulfate in scrubber 2 gr | % S absorbed in IL % |
|---|---|---|---|
| 6A | 0.058 | 0.049 | 54 |
| 6B | 0.006 | 0.039 | 13 |

Example 7—Separation of Mercury and Sulfide from Ionic Liquid in Presence of Iodine Ionic liquid containing $HgI_2$ and access of iodine: the ionic liquid was 1-butyl-3-methylimidazolium bromide (BMIM-Br), comprising about 1.5% wt iodine ($I_2$) and 0.48% $HgI_2$. The amount of 0.776 gr iodine was dissolved in 50 gr of the ionic liquid containing 0.242 gr of $HgI_2$ at room temperature.

An amount of 1.1 gr of sodium sulfide hexahydrate (35% $Na_2S$) was added into the ionic liquid solution to furnish concentration of about 0.74 M. A black particles appeared in the bottom of the ionic solution. Thereafter, a 61 mL of water was added into the IL. A yellow/black precipitate was formed. The solid was filtered by vacuum and weighed: 0.36 gr (dry weight) of elemental sulfur mix with mercury sulfide was found (~100% conversion).

Iodine was recovered by additional process: 1) The excess of water was evaporated at 90° C. for 1.5 hours; 2) The pH was adjusted by adding of HCl 8.2 mL solution (1N), to about 6.5; 3) The regenerating oxidant—hydrogen peroxide, 0.9 mL of 35% w/v solution, was then added, and the water access was evaporated at 90° C.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A process for purification of an ionic liquid from heavy metals, comprising combining heavy metal-containing ionic liquid and a sulfide source to form heavy metal sulfide, and separating said heavy metal sulfide from the ionic liquid.

2. The process according to claim 1, wherein the ionic liquid contains the heavy metal in the form of a halide salt prior to the addition of the sulfide source.

3. The process according to claim 1, wherein said sulfide source is hydrogen sulfide, ammonium sulfide, or an alkali metal sulfide.

4. The process according to claim 1, wherein the heavy metal sulfide is separated from an essentially water-free ionic liquid.

5. The process according to claim 4, wherein the heavy metal sulfide is precipitated in, and separated from, an ionic liquid that comprises no more than 5 weight percent of water.

6. The process according to claim 1, wherein the heavy metal sulfide is separated from an aqueous ionic liquid mixture, wherein the aqueous ionic liquid mixture is generated by diluting the ionic liquid with water subsequent to the addition of the sulfide source.

7. The process according to claim 6, wherein water is added to a concentration of between 25 and 60 weight percent in the aqueous ionic liquid mixture.

8. The process according to claim 1, wherein the heavy metal is mercury and the ionic liquid is 1-alkyl-3-methylimidazolium halide.

9. A process of regeneration of spent scrubbing liquid suitable for removal of heavy metals from a gas, wherein said spent liquid comprises an ionic liquid, a heavy metal species and a reduced oxidant species, said process comprises sequentially combining said spent scrubbing liquid with a sulfide source, whereby an heavy metal sulfide is formed, and with a regenerating oxidizing agent, whereby said reduced oxidant species is regenerated into active oxidant species.

10. The process according to claim 9, further comprising separating said heavy metal sulfide from the ionic liquid before the addition of the oxidizing agent.

11. The process according to claim 9, wherein the ionic liquid is 1-alkyl-3-methylimidazolium halide, the heavy metal is mercury and the reduced oxidant species is a halide selected from bromide or iodide.

12. A process of decontamination a gaseous stream from sulfides, said process comprising passing said stream through an essentially water-free water-miscible ionic liquid, and adding water to said essentially water-free water-miscible ionic liquid, in presence of an oxidant, thereby converting sulfides into elemental sulfur and/or sulfates.

13. The process according to claim 12, further comprising separating said elemental sulfur from the ionic liquid by filtration, centrifugation or decantation.

14. The process according to claim 12, wherein said water is added to a concentration of between 15 and 60 weight percent.

15. The process according to claim 12, wherein said oxidant is bromine or iodine.

16. The process of claim 12, further comprising the steps of recycling a spent scrubbing liquid formed during decontamination of said gaseous stream, said recycling comprising reducing the pH of the ionic liquid to below 7, oxidizing the halide into elemental halogen by providing a regenerating oxidizing agent, and removing water from the ionic liquid.

17. A process of decontamination a gaseous stream from sulfides and heavy metals, said process comprising the steps of:
passing said stream through a scrubbing liquid comprising an essentially water-free water-miscible ionic liquid and an oxidant reducible into a halide, and
either in the presence of indigenously formed heavy metal halide or of an added heavy metal halide, introducing water to said essentially water-free water-miscible ionic liquid,
thereby precipitating heavy metal sulfides and converting excess sulfides into elemental sulfur and/or sulfates.

18. The process according to claim 17, wherein the sulfide in the gas stream is $H_2S$, the heavy metal in the gas stream is mercury, the ionic liquid is 1-alkyl-3-methylimidazolium halide and the oxidant is iodine.

19. The process according to claim 17, wherein said oxidant is bromine or iodine.

20. The process according to claim 17, further comprising determining if a molar ratio between said heavy metal halide and sulfide is higher than 1, determining the amount of sulfide required to bring the ratio to below 1, and adding the determined amount of sulfide into said mixture, prior to said adding of water.

* * * * *